United States Patent [19]

Thomashow

[11] Patent Number: 5,356,816
[45] Date of Patent: Oct. 18, 1994

[54] METHOD AND COMPOSITIONS USING POLYPEPTIDES OF ARABIDOPSIS THALIANA

[75] Inventor: Michael F. Thomashow, East Lansing, Mich.

[73] Assignee: Board of Trustees Operating Michigan State University, East Lansing, Mich.

[21] Appl. No.: 2,886

[22] Filed: Jan. 11, 1993

Related U.S. Application Data

[62] Division of Ser. No. 794,398, Nov. 19, 1991.

[51] Int. Cl.$^5$ ............... C07H 17/00; A61K 35/78
[52] U.S. Cl. .................. 435/320.1; 536/23.6; 530/370; 530/379
[58] Field of Search ............... 514/2, 12; 435/320.1; 536/23.6; 530/350, 370, 379

[56] References Cited

PUBLICATIONS

Thomashow, M. F., Adv. Genet. 28:99–131 (1990).
Steponkus, P. L., Cold acclimation and freezing injury from a perspective of the plasma membrane. In Katterman, F. (ed), Environmental Injury to Plants pp. 1–16, Academic Press, San Diego (1990).
Steponkus, P. L., et al., Proc. Nalt. Acad. Sci. USA 85: 9026–9030 (1988).
Weiser, C. J., Science 169: 1269–1278 (1970).
Volger, H. G., et al., Biochim. Biophys. Acta 412: 335–349 (1975).
Hincha, D. K., et al., Plant Physiol. Biochem. 27: 795–801 (1989).
Hincha, D. K., et al., Planta 180: 416–419 (1990).
Gilmour, S. J., et al., Plant Physiol. 97: 745–750 (1988).
Lin, C., et al., Plant Physiol. 94:1078–1083 (1990).
Hajela, R. K., et al., Plant Physiol, 93:1246–1252 (1990).
Sanger, F., et al., Proc. Natl. Acad. Sci. USA 74:5463–5467 (1977).
Tamiya, T., et al., Cryobiology 22: 446–456 (1985).
Thomashow, M. F., et al., Horticultural Biotechnology, pp. 305–314 (1990).
Davis, P. L., et al., FASEB (Biochemistry of fish antifreeze proteins), 2460–2468 (1990).
Suggs et al. PNAS, vol. 78, No. 11, pp. 6613–6617, Nov. 1981.

Primary Examiner—Robert A. Wax
Assistant Examiner—Keith D. Hendricks
Attorney, Agent, or Firm—Ian C. McLeod

[57] ABSTRACT

A method for treating chemical or biological materials with a polypeptide derived from a RNA encoded by a cDNA of *Arabidopsis thaliana* to prevent freezing or heat damage is described. In particular, a novel cDNA and polypeptide, COR15, encoded thereby is described.

2 Claims, 2 Drawing Sheets

METHOD AND COMPOSITIONS USING POLYPEPTIDES OF ARABIDOPSIS THALIANA

This application was funded under United States Department of Agriculture Contract 88-37264-3880. The U.S. Government has certain rights under the application and any patent issuing thereon.

This is a divisional of copending application Ser. No. 07/794,398 filed on Nov. 19, 1991.

BACKGROUND OF THE INVENTION (1) Field of the Invention

The present invention relates to the use of polypeptides which prevent freezing damage to materials and which are derived from cDNA's of RNA's isolated from *Arabidopsis thaliana* which have been exposed to near freezing temperatures or which have been treated with abscisic acid. The resulting polypeptides are cryoprotective to chemical and biological materials. In particular the present invention relates to a preferred 15 kilodalton polypeptide, referred to as COR15, which is cryoprotective.

(2) Prior Art

In many species of higher plants, a period of exposure to low non-freezing temperatures results in an increased level of freezing tolerance (Thomashow, M. F., Adv. Genet. 28: 99-131 (1990)). Davies FASEB Journal 4, 2460-2468 (1990) describes fish antifreeze proteins. Considerable effort has been directed at understanding the molecular basis of this cold acclimation response, yet the mechanism remains poorly understood. A large number of biochemical changes have been shown to be associated with cold acclimation including alterations in lipid composition, increased sugar and soluble protein content, and the appearance of new isozymes (Thomashow, M. F., Adv. Genet. 28: 99-131 (1990); and Steponkus, P. L., Cold acclimation and freezing injury from a perspective of the plasma membrane. In Katterman, F. (ed), Environmental Injury to Plants pp 1-16. Academic Press, San Diego (1990)). However, in most cases, the exact role and relative importance that a given change has in cold acclimation remains uncertain. A notable exception regards certain changes in lipid composition. Steponkus and colleagues (Steponkus, P. L., et al., Proc. Natl. Acad. Sci. USA 85: 9026-9030 (1988)) have presented data indicating that specific changes in the phospholipid composition of rye cell plasma membranes dramatically alters the cryobehavior of the membranes and contributes directly to the increased freezing tolerance of acclimated cells.

In 1970, Weiser (Weiser, C. J., Science 169: 1269-1278 (1970)) suggested that cold acclimation might involve changes in gene expression. Since then, it has been clearly established that changes in gene expression occur during cold acclimation in a wide range of plant species (Thomashow, M. F., Adv. Genet. 28: 99-131 (1990) and Thomashow, M. F., et al, Horticultural Biotech 305-314 (1990)). Efforts are now being directed at determining the functions of these cold-regulated genes. One interesting possibility is suggested by the work of Heber and colleagues (Volger, H. G., et al., Biochim. Biophys. Acta 412: 335-349 (1975); Hincha, D. K., et al., Plant Physiol. Biochem. 27: 795-801 (1989); Hincha, D. K., et al., Planta 180: 416-419 (1990)). These investigators have shown that cold acclimated spinach and cabbage, but not nonacclimated plants, synthesize hydrophilic, heat-stable, low molecular weight polypeptides (10-20 kd) that have cryoprotective properties. In particular, these polypeptides, which have not been purified or individually identified, were reported to be greater than 10,000 times (molar basis) more effective in protecting thylakoid membranes against freezing damage in an in vitro assay than were known low molecular weight cryoprotectants such as sucrose. Whether these polypeptides contribute significantly to the increased freezing tolerance of cold acclimated plants in vivo remains to be determined.

It has been established that Arabidopsis becomes more tolerant to freezing temperatures when exposed to low non-freezing temperatures and that changes in gene expression occur during the cold acclimation process (Gilmour, S. J., et al., Plant Physiol. 97: 745-750 (1988)). It has been reported that four Arabidopsis cor (cold-regulated) genes encode polypeptides, 160, 47, 24, and 15 kDa in mass, that share an unusual biochemical property: they remain soluble upon boiling in aqueous solution (Lin, C., et al., Plant Physiol. 94: 1078-1083 (1990)). In addition, it has been found that wheat also has cot genes that encode "boiling-stable" polypeptides and that wheat has a cor gene(s) that is related to Arabidopsis COR47, a cold-regulated gene that encodes a 47 kDa boiling-stable polypeptide (Lin, C., et al., Plant Physiol. 94: 1078-1083 (1990)). It has been suggested it is likely that the boiling-stable COR polypeptides of Arabidopsis and wheat have a fundamental role in plants acclimating to cold temperatures (Lin, C., et al., Plant Physiol. 94: 1078-1083 (1990)). In addition, it has been speculated (Lin, C., et al., Plant Physiol. 94: 1078-1083 (1990)) that these polypeptides might be analogous to the cryoprotective polypeptides described by Heber and colleagues (Volger, H. G., et al., Biochim. Biophys. Acta 412:335-349 (1975); Hincha, D. K., et al., Plant Physiol. Biochem. 27:795-801 (1989); and Hincha, D. K., et al., Planta 180: 416-419 (1990)).

There has been no suggestion that the genes encoding these cold "regulated" polypeptides might be synthesized and used to protect various materials. The problem has been to provide DNA which encodes the polypeptides.

OBJECTS

It is therefore an object of the present invention to provide a method which uses polypeptides from *Arabidopsis thaliana* to prevent freezing damage. Further still, it is an object of the present invention to provide a novel preferred cDNA which encodes a polypeptide which is cryoprotective and a method of use of the polypeptides. These and other objects will become increasingly apparent by reference to the following description and the drawings.

IN THE DRAWINGS

GENERAL DESCRIPTION

Figures 1A, 1B:
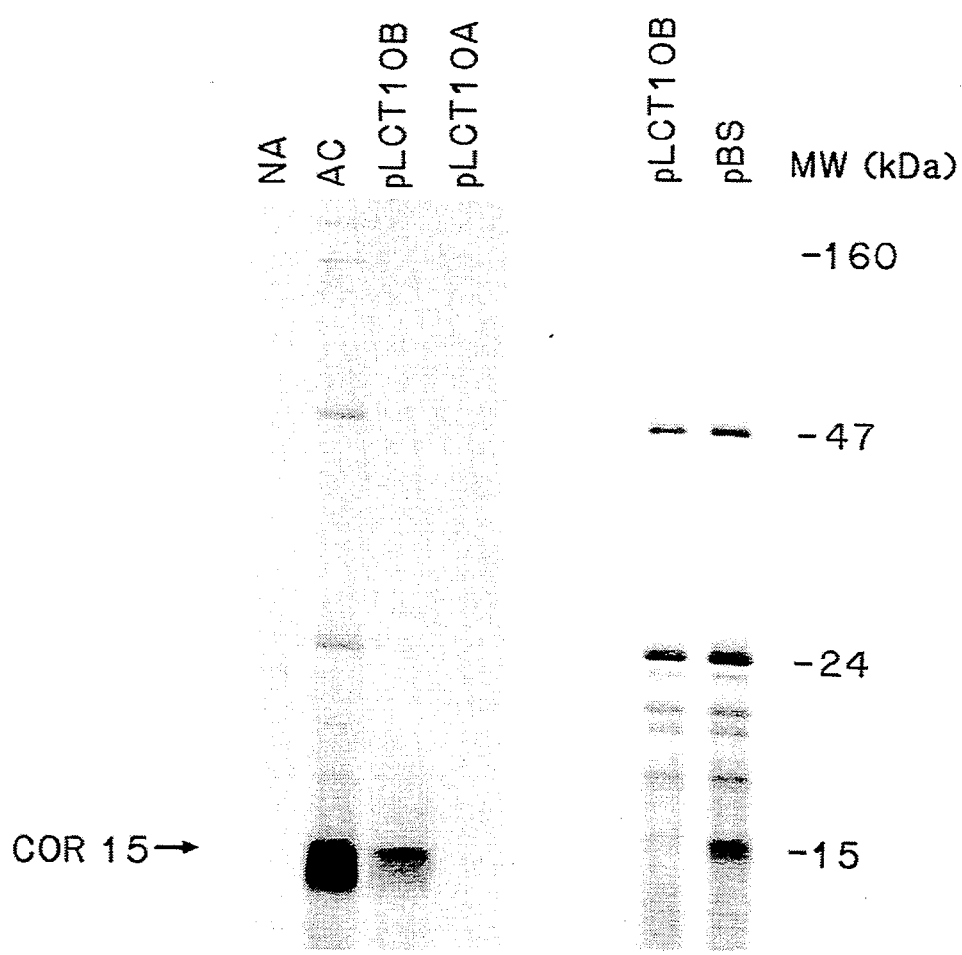
FIG. 1 is an electrophoresis gel showing that plasmid pLCT10B contains a cDNA insert encoding a preferred 15KD boiling-stable polypeptide designated as COR15.

The present invention relates to a method for protecting chemical or biological materials from freezing damage which comprises applying a polypeptide homologous to a polypeptide encoded by an RNA of *Arabidopsis thaliana* subjected to near freezing temperatures wherein the polypeptide prevents the freezing damage to the chemical and biological material.

In particular, the present invention relates to a method for preventing freezing damage to a biological or chemical material which comprises applying a polypeptide homologous to a polypeptide encoded by RNA isolated as a result of subjecting *Arabidopsis thaliana* to near freezing temperatures or abscisic acid and selected from the group consisting of polypeptide-1 and polypeptide-2, polypeptide-3 and polypeptide-4, and polypeptide 5 which are 6.6, 15, 24, 47 and 160 kilodaltons in mass, respectively, mixtures thereof and fragments thereof and which are stable upon boiling in water and which are cryoprotective with the biological or chemical materials to prevent the freezing damage when admixed.

Further, the present invention relates to a cDNA having a sequence which comprises:

which comprises: applying a polypeptide homologous to an RNA isolated from *Arabidopsis thaliana* subjected to near freezing temperature or to abscisic acid to the material in an amount sufficient to inhibit the water stress damage.

The present invention also relates to a method for preventing damage caused by "water stress" (drought, water loss, desiccation, lyophilization) in a material which comprises: applying a polypeptide homologous to RNA isolated as a result of subjecting *Arabidopsis thaliana* to near freezing temperatures or abscisic acid and selected from the group consisting of polypeptide-1 and polypeptide-2, polypeptide-3 and polypeptide-4, polypeptide-5 which are 616, 15, 24, 47 and 160 kilodaltons in mass, respectively, mixtures thereof and fragments thereof and which are stable upon boiling in water and which are cryoprotective in an amount sufficient to inhibit water stress damage to the material.

```
  1 AAA AAC TCC TCC TTT CAT TTC CAA ACA AAA ACT TCT TTT TAT TC-
T CAC 48

49 ATC TTA AAG ATC TCT CTC ATG GCG ATG TCT TTC TCA GGA GCT GTT CTC  96
                            Met Ala Met Ser Phe Ser Gly Ala Val Leu  10
                                             5                       10

97 ACT GGT ATG GCT TCT TCT TTC CAC AGC GGA GCC AAG CAG AGC AGC TTC 144
 11 Thr Gly Met Ala Ser Ser Phe His Ser Gly Ala Lys Gln Ser Ser Phe  26
                        15                  20                  25

145 GGC GCT GTC AGA GTC GGC CAG AAA ACT CAG TTC GTC GTC GTT TCT CAA 192
 27 Gly Ala Val Arg Val Gly Gln Lys Thr Gln Phe Val Val Val Ser Gln  42
                30                  35                  40

193 CGC AAG AAG TCG TTG ATC TAC GCC GCT AAA GGT GAC GGC AAC ATC CTC 240
 43 Arg Lys Lys Ser Leu Lle Thr Ala Ala Lys Gly Asp Gly Asn Ile Leu  58
                45                  50                  55

241 GAT GAC CTC AAC GAG GCC ACA AAG AAA GCT TCA GAT TTC GTG ACG GAT 288
 59 Asp Asp Leu Asn Glu Ala Thr Lys Lys Ala Ser Asp Phe Val Thr Asp  74
                60                  65                  70

289 AAA ACA AAA GAG GCA TTA GCA GAT GGT GAG AAA GCG AAA GAC TAC GTT 336
 75 Lys Thr Lys Glu Ala Leu Als Asp Gly Glu Lys Ala Lys Asp Tyr Val  90
        75          .       80                  85                  90

337 GTT GAA AAA AAC AGT GAA ACC GCA GAT ACA TTG GGT AAA GAA GCT GAG 384
 91 Val Glu Lys Asn Ser Glu Thr Ala Asp Thr Leu Gly Lys Glu Ala Glu 106
                95                  100                 105

385 AAA GCT GCG GCG TAT GTG GAG GAG AAA GGA AAA GAA GCC GCA AAC AAG 432
107 Lys Ala Ala Ala Tyr Val Glu Glu Lys Gly Lys Glu Ala Ala Asn Lys 122
                110                 115                 120

433 GCG GCA GAG TTC GCG GAG GGT AAA GCA GGA GAG GCT AAG GAT GCC ACA 480
123 Ala Ala Glu Phe Ala Glu Gly Lys Ala Gly Glu Ala Lys Asp Ala Thr 138
                125                 130                 135

481 AAG TAG GGT CTT ACC TAA TCA GTT AAT TTC AAG CAC TTA AAC TCG TAG 528
139 Lys

529 ATA TAT TGA TCC ATA TCC TCT CTC TTC ATG TTT AAT AGT ACT-
TAC AAT 576

577 AAG ATG AGT CTG TTG TAA TTT CTA TTA ATT TCA CAT CAC AAC T-
GA AAT 624

625 AAG ATA TGG TAT CCA CAG TCA CCG TCA CAT TCT TTA ATG TTT T-
GC AAA 672

673 ATA TTC AAT AGA CAA ATT AAA TAA AAA AAA AAA AAA
``` and fragments thereof, wherein the cDNA and the fragments encode polypeptides which are cryoprotective to prevent freezing damage to biological and chemical materials.

Further the present invention relates to a method for inhibiting water stress damage to a biological material Further, the present invention relates to a composition which comprises a biological material in need of protection against freezing or water stress damage; and a polypeptide homologous to a RNA isolated from *Arabidopsis thaliana* subjected to near freezing temperatures or abscisic acid in an amount sufficient for protection between about $10^{-3}$ and $10^5$ part per part of the material.

The present invention particularly relates to a preferred cDNA derived from RNA of *Arabidopsis thaliana* as contained in a plasmid referred to as pLCT10B and deposited under the Budapest Treaty as ATCC 75139 with the American Type Culture Collection in Rockville, Md.

The biological materials can be proteins, cells (plant and animal), bacteria, fungi and materials isolated from natural sources which may be damaged by freezing. The chemical products can be various compounds which are injured by freezing, such as polymers and the like, particularly where the materials contain water which tends to crystalize upon freezing and damage the material. The material can be dried or frozen. Preferably the polypeptide is used in an amount between about $10^{-3}$ and $10^5$ parts per part of the material to be protected by weight.

The polypeptides of the present invention also have the ability to inhibit water stress damage in living biological materials, particularly whole plants, cells of plants or animals and microorganisms (bacteria, fungi and virus). The compounds are particularly effective when applied to whole plants in preventing drought damage. The stability of the polypeptide to heating is an advantage in use. The compounds are used in amounts between about $10^{-3}$ and $10^5$ per gram of the biological material.

SPECIFIC DESCRIPTION

An Arabidopsis cDNA clone for COR15, the gene that encodes the boiling-stable 15 kDa polypeptide was identified. DNA sequence analysis indicated that COR15 is 14,604 daltons in mass and is hydrophilic. In addition, biochemical analysis indicated that COR15 has potent cryoprotective activity in an in vitro assay; on a molar basis, COR15 was approximately $10^8$ times more effective than sucrose in protecting lactate dehydro-genase against inactivation by a freeze-thaw cycle.

EXAMPLE 1

Materials and Methods cDNA clones pLCT10A and pLCT10B are homologous to a previously described cot cDNA clone, pHH67 (Hajela, R. K., et al., Plant Physiol. 93: 1246-1252 (1990). Both pLCT10A and pLCT10B have the same 709 bp EcoRI insert cloned in the EcoRI site of pBluescript SK−, but in opposite orientations. pLCT10A was isolated by screening plaque lifts of a cDNA library for recombinant phage that hybridized with the insert from pHH67; probes were prepared by nick translation or random priming (Hajela, R. K., et al. Plant Physiol. 93: 1246-1252 (1990)). The cDNA library screened was prepared from poly(A+) RNA isolated from *Arabidopsis thaliana* Columbia seedlings that had been grown at 22° C. for approximately 15 days and cold acclimated at 5° C. for 3 days. The cDNA library was constructed in lambda ZAP (Stratagene) as previously described (Hajela, R. K., et al., Plant Physiol. 93: 1246-1252 (1990)). Recombinants carrying inserts related to pHH67 were plaque purified and the inserts "subcloned" into pBluescript SK− by biological rescue (Hajela, R. K., et al., Plant Physiol. 93: 1246-1252 (1990)). One of the clones chosen for further study was pLCT10A. The orientation of the EcoRI insert in pLCT10A was reversed as follows to yield pLCT10B=phagemid DNA was digested with EcoRI, the mixture relegated with T4 ligase and transformed into *Escherichia coli*, and the desired clone identified by restriction analysis. DNA sequence analysis indicated that the insert of pLCT10A and pLCT10B represented the same gene as pHH67, but had additional sequences from the 5' end of the transcript.

DNA sequencing

The DNA sequence of the DNA insert in pLCT10A and pLCT10B was determined by the Sanger dideoxy-method (Sanger, F., et al., Proc. Natl. Acad. Sci. USA 74: 5463-5467 (1977)) using (U.S. Sequenase Biochemicals, Cleveland, Ohio), according to the manufacturer's instructions. Deletions of the insert were generated using exonuclease III. The complete sequence of each strand of the insert was determined. Sequence analysis was done using the PROsis and DNAsis programs of Hitachi and the CGC programs of the University of Wisconsin Biotechnology Center.

Hybrid-arrest/in vitro translation reactions

PolyA+RNA was isolated from cold acclimated plants (Gilmour, S. J., et al., Plant Physiol. 97:745-750 (1988); Lin, C, et al., Plant Physiol. 94: 1078-1083 (1990); and Hajela, R. K., et al., Plant Physiol. 93: 1246-1252 (1990)) and hybridized with single-stranded DNA prepared from pLCT10B and pBluescript. The "arrest" reactions were translated in vitro using a rabbit reticulocyte lysate system (Promega, Madison, Wis.) with [$^{35}$S]methionine as radiolabel. The resulting radioactive polypeptides were fractionated by SDS-PAGE and visualized by autoradiography as previously described (Lin, C., et al., Plant Physiol. 94: 1078-1083 (1990)).

In vitro transcription/translation reactions pLCT10A and pLCT10B were linearized by digestion with BamHI and the inserts transcribed in vitro with T7 RNA polymerase (Stratagene) using the T7 promoter carried on the pBluescript vector. The resulting transcripts were then translated in vitro as described above.

Preparation of COR15 pLCT10B was transcribed and translated in vitro (as described above) and the resulting translation mix containing [$^{35}$S]COR15 was boiled for 10 minutes and centrifuged 15 minutes in an Eppendorf centrifuge to remove insoluble material (which included most of the proteins present in the in vitro translation mix). The boiling-soluble fraction, which contained the [$^{35}$S]COR15 polypeptide, was fractionated by SDS-PAGE using 15% (w/v) polyacrylamide gels and the COR15 polypeptide was located using a Betagen 603 Blot Analyzer. The region of the gel containing the COR15 polypeptide was excised with a razor blade and the polypeptide recovered by electroelution (CBS Science Inc., Del Mar, Calif.). The sample was then electrodialyzed against 20 mM Tris-HCl (pH 8.9) for 24 hours at 150 V, and precipitated with acetone. The amount of COR15 obtained was estimated based on the total dpm of the preparation, the specific activity of the [$^{35}$S]methionine used in the in vitro translation reaction, and the number of methionine residues per polypeptide as deduced from the sequence. The yields of COR15 in three experiments ranged from 0.4 μg to 1.5 μg. As a control for the cryoprotection assays, mock preparations of COR15 were made using transcripts prepared from pLCT10A. In this case, the region of the SDS- PAGE gels that corresponded to the position of the [$^{35}$S]COR15 produced in the above reactions was excised and treated the same as the COR15 samples.

The relative cryoprotective activities of COR15, sucrose and various proteins were assayed using the freeze-labile enzyme lactate dehydrogenase (LDH) (rabbit muscle M4 enzyme obtained from Sigma) essentially as described by Tamiya, et al. (Tamiya, T., et al., Cryobiology 22: 446–456 (1985)). A solution of LDH (1.25 μg/ml; rabbit muscle M4 enzyme obtained from Sigma) was prepared in 10 mM potassium phosphate buffer pH7.5. 50 μl of this solution was placed in a plastic microcentrifuge tube (Eppendorf) and 50 μl of the test compound suspended in 10 mM potassium phosphate buffer pH 7.5 was added. The LDH/additive mixtures were frozen at −20° C. for 24 hours and thawed at room temperature for 5 to 10 minutes. The LDH activity of the initial enzyme solution and the samples that had been frozen and thawed were assayed essentially as described by Tamiya et al. (Tamiya, T., et al., Cryobiology 22: 446–456 (1985)). Briefly, 20 μl of sample was added to 1 ml of assay mix (at room temperature) which contained 80 mM Tris-HCl pH7.5, 100 mM KCl, 2 mM pyruvic acid and 0.3 mM NADH. The absorbance decrease at 340 nm was measured (at room temperature) using a recording scanning spectrophotometer. The rate of decrease in absorbance during the first 3 minutes of the reaction was used to calculate LDH activity (rates were linear over this time interval). All samples were assayed in triplicate. The $CP_{50}$ value was defined as the concentration of the additive required to protect 50% of the LDH activity from freeze-inactivation. The proteins alpha-lactalbumin, lysozyme, bovine serum albumin (BSA), and RNase A were purchased from Sigma (St. Louis, Mo.).

RESULTS

Identification of a cDNA clone encoding COR15. cDNA clones of four Arabidopsis cor genes (Hajela, R. K., et al., Plant Physiol. 93: 1246–1252 (1990)) were isolated. Preliminary hybrid-select in vitro translation experiments with one of the clones, pHH67, indicated that it encoded the boiling-stable COR15 polypeptide. Further experiments with pLCT10A and pLCT10B, cDNA clones homologous to pHH67, confirmed these results (see Materials and Methods). Hybrid-arrest in vitro translation experiments indicated that pLCT10B hybridized with the transcript encoding the boiling-stable COR15 polypeptide; the COR15 polypeptide was observed when the pBluescript vector was used in the hybrid-arrest reaction, but was not observed when pLCT10B was used (FIG. 1B). Further, when pLCT10B was transcribed and translated in vitro, a polypeptide of 15 kd was produced (FIG. 1A). This polypeptide remained soluble upon boiling. When pLCT10A was transcribed and translated in vitro, no boiling stable polypeptides were produced (FIG. 1A).

DNA sequence analysis. The DNA sequence of the cDNA insert cloned in pLCT10A and pLCT10B was determined. Analysis of the data indicated that the sequence contained an open reading frame that would encode a 140 amino acid long polypeptide with a predicated molecular weight of 14,604 daltons. The polypeptide had a high alanine (17.9 mol %) and lysine (14.3 mol %) content and was devoid of cysteine, tryptophan and proline residues. The polypeptide was hydrophilic having a mean hydrophobic index of −0.6.

Computer searches of the Genbank EMBL data bases (release 6.0) did not reveal any extensive nucleic acid or amino acid sequence homology between the cor15 gene or polypeptide and previously sequenced genes or polypeptides.

Figure 2:
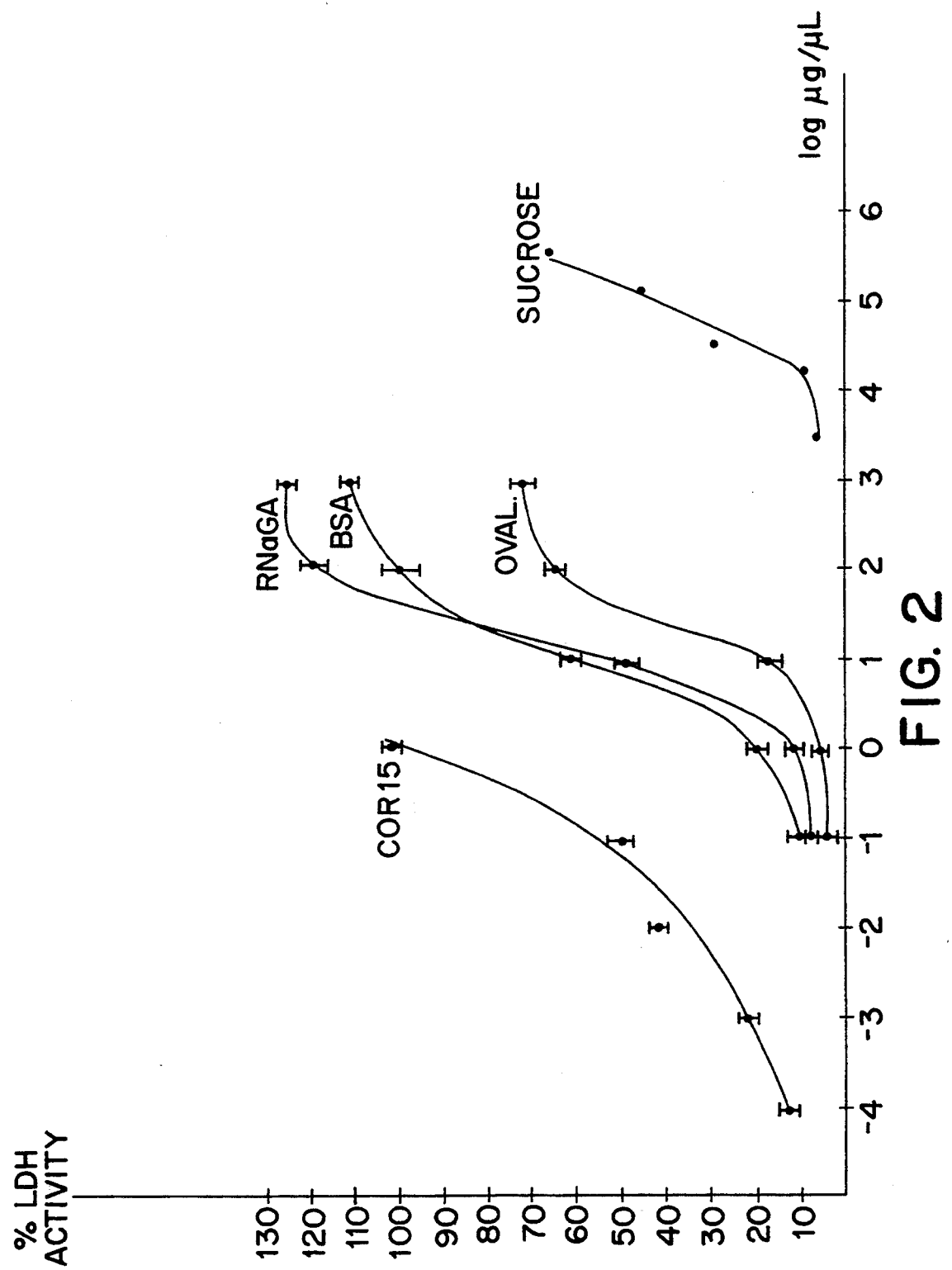
FIG. 2 is a graph showing the cryoprotective activity of COR15 and other proteins/chemicals in admixture with lactate dehydrogenase.

COR15 has cryoprotective activity in vitro. It was determined whether COR15 had cryoprotective activity in an in vitro assay. Specifically, it was determined whether COR15 could protect lactate dehydrogenase from freeze inactivation; lactate dehydrogenase is a freeze labile enzyme that is commonly used to determine whether a given molecule has cryoprotective activity (Tamiya, T., et al., Cryobiology 22: 446–456 (1985)). The COR15 used in the assay was prepared by transcribing pLCT10B in vitro, translating the RNA using the rabbit reticulocyte system, and purifying the polypeptide by SDS-PAGE (see Materials and Methods for details). The results of the protection assays indicated that COR15 did indeed have cryoprotective activity as shown by Table 1 and FIG. 2. On a molar basis, COR15 was approximately $10^8$ times more effective than sucrose in protecting lactate dehydrogenase from freeze inactivation.

Previous studies have indicated that BSA (Tamiya, et al., Cryobiology 22, 446–456 (1985)) could protect lactate dehydrogenase from freeze inactivation. It was, therefore, of interest to determine the relative effectiveness of COR15 and BSA in protecting lactate dehydrogenase from freezing. The data indicated that the CP50 of BSA was approximately 10 μg/ml. Thus, on a molar basis, COR15 was approximately 100 times more effective than BSA. A number of other proteins that are relatively hydrophilic, including RNAse A which is heat-stable, were also tested and found to have cryoprotective activity. However, these proteins were about 100 to 1000 fold less effective than COR15 (Table 1).

TABLE 1

| Additives | $P_{50}$ (μg/ml) | $CP_{50}$ (M × $10^{-5}$) | Comparison with COR15 on Molar basis (average) |
|---|---|---|---|
| COR15 (14,600) | 0.66 ± 0.003 | 4.50 ± 0.20 | 1.0 |
| | 0.82 ± 0.010 | 5.62 ± 0.70 | |
| HP - 0.6 | 0.100 ± 0.005 | 6.80 ± 0.30 | |
| | 0.100 | 6.80 | |
| RNase A (13,700) | 13.7 ± 2.10 | 1,000 ± 150 | 5.6 × $10^{-3}$ |
| | 14.0 ± 2.80 | 1,021 ± 208 | |
| HP - 0.0 | 20.9 ± — | 1,525 ± — | |
| beta-gal (116,000) | 107.0 ± 6.2 | 927 ± 54 | 4.9 × $10^{-3}$ |
| | 147.0 ± 17.2 | 1,270 ± 148 | |
| HP - 0.0 | 174.0 ± 14.2 | 1,500 ± 122 | |
| oval (45,000) | 51.8 ± 5.1 | 1,151 ± 113 | 3.1 × $10^{-3}$ |
| | 81.6 ± 8.3 | 1,813 ± 186 | |
| HP + 0.1 | 115.3 ± 21.3 | 2,562 ± 474 | |
| BSA (66,000) | 5.7 ± 0.2 | 86.3 ± 3.2 | 63.4 × $10^{-3}$ |
| | 10 ± — | 151 ± — | |
| | 23.7 ± 2.3 | 358 ± 34 | |
| try. in (20,100) | 34.7 ± — | 1,726 ± | 0.9 × $10^{-3}$ |
| | 61.4 ± 5.7 | 3,054 ± 285 | |
| HP - 0.1 | 267 ± 19 | 13,298 ± 939 | |
| sucrose (340) | (22 ± 0.7) × $10^4$ | (0.64 ± 0.02) × $10^9$ | 6.7 × $10^{-9}$ |
| | (28 ± 1.0) × $10^4$ | (0.82 ± 0.03) × $10^9$ | |
| | (32 ± 3.0) × $10^4$ | (0.94 ± 0.09) × $10^9$ | |
| 2-1 ac | 9.9 ± 9.4 | 697 ± 664 | 6.4 × $10^{-3}$ |
| lysozyme (14,000) | 12.5 ± — | 1,800 ± — | 52 × $10^{-3}$ |

DISCUSSION

The results of Example 1 indicate that the cold-regulated COR15 polypeptide of Arabidopsis is hydrophilic, is boiling-stable, and has potent cryoprotective activity in a standard in vitro assay. Thus, COR15 has characteristics in common with the ill defined cryoprotective polypeptides described by Heber, Hincha and colleagues (Volger, H. G., et al., Biochim. Biophys. Acta 412: 335–349 (1975); Hincha, D. K., et al., Plant Physiol. Biochem. 27: 795–801 (1989); and Hincha, D. K., et al., Planta 180 416–419 (1990)). These later crude preparations of polypeptides, which have been found in both spinach and cabbage, but have not yet been purified, are also cold-regulated (they are detected in cold acclimated but not nonacclimated plants), they are hydrophilic, they remain soluble and active upon boiling, and they have cryoprotective activity in an in vitro assay; they protect thylakoid membranes (in vitro) from rupture induced by a freeze-thaw cycle.

The finding that COR15 has potent cryoprotective activity in vitro suggests a role for this polypeptide in cold acclimation; the polypeptide might serve to protect proteins and possibly membranes from damage induced by a freeze-thaw cycle. There is no direct evidence that COR15 in nature has a cryoprotective role in vivo. The creation of Arabidopsis mutants that either underexpress or overexpress COR15 will substantiate the function of this polypeptide and its relative importance to the cold acclimation process.

In the same manner other homologous cold-regulated polypeptides can be synthesized. These polypeptides may also have cryoprotective properties.

In the same manner, materials can be protected from water stress by applying or mixing the polypeptides. The material can be living or it can be a chemical or biochemical.

Attached is Appendix I for the cDNA carried in plasmid pLCT10B deposited as ATCC 75139.

It is intended that the foregoing description be only illustrative of the present invention and that the present invention be limited only by the hereinafter appended claims.

I claim:

1. A cDNA encoding a 15 kilodalton polypeptide having a sequence:

```
1   AAA  AAC  TCC  TCC  TTT  CAT  TTC  CAA  ACA
               AAA  ACT  TCT  TTT  TAT  TCT  CAC   48

49  ATC  TTA  AAG  ATC  TCT  CTC  ATG  GCG  ATG
                                   Met  Ala  Met
               TCT  TTC  TCA  GGA  GCT  GTT  CTC   96
               Ser  Phe  Ser  Gly  Ala  Val  Leu
                5                        10

97  ACT  GGT  ATG  GCT  TCT  TCT  TTC  CAC  AGC
11  Thr  Gly  Met  Ala  Ser  Ser  Phe  His  Ser
                              15
               GGA  GCC  AAG  CAG  AGC  AGC  TTC   144
               Gly  Ala  Lys  Gln  Ser  Ser  Phe   26
                20                       25

145 GGC  GCT  GTC  AGA  GTC  GGC  CAG  AAA  ACT
27  Gly  Ala  Val  Arg  Val  Gly  Gln  Lys  Thr
                    30                    35
               CAG  TTC  GTC  GTC  GTT  TCT  CAA   192
               Gln  Phe  Val  Val  Val  Ser  Gln   42
                                        40

193 CGC  AAG  AAG  TCG  TTG  ATC  TAC  GCC  GCT
43  Arg  Lys  Lys  Ser  Leu  Ile  Thr  Ala  Ala
                    45                    50
               AAA  GGT  GAC  GGC  AAC  ATC  CTC   240
               Lys  Gly  Asp  Gly  Asn  Ile  Leu   58
                              55

241 GAT  GAC  CTC  AAC  GAG  GCC  ACA  AAG  AAA
59  Asp  Asp  Leu  Asn  Glu  Ala  Thr  Lys  Lys
                    60                    65
               GCT  TCA  GAT  TTC  GTG  ACG  GAT   288
               Ala  Ser  Asp  Phe  Val  Thr  Asp   74
                              70

289 AAA  ACA  AAA  GAG  GCA  TTA  GCA  GAT  GGT
75  Lys  Thr  Lys  Glu  Ala  Leu  Ala  Asp  Gly
                    75                    80

GAG  AAA  GCG  AAA  GAC  TAC  GTT   336
               Glu  Lys  Ala  Lys  Asp  Tyr  Val   90
                               85                  90

337 GTT  GAA  AAA  AAC  AGT  GAA  ACC  GCA  GAT
91  Val  Glu  Lys  Asn  Ser  Glu  Thr  Ala  Asp
                                   95
               ACA  TTG  GGT  AAA  GAA  GCT  GAG   384
               Thr  Leu  Gly  Lys  Glu  Ala  Glu   106
                100                      105

385 AAA  GCT  GCG  GCG  TAT  GTG  GAG  GAG  AAA
107 Lys  Ala  Ala  Ala  Tyr  Val  Glu  Glu  Lys
                              110
               GGA  AAA  GAA  GCC  GCA  AAC  AAG   432
               Gly  Lys  Glu  Ala  Ala  Asn  Lys   122
                115                      120

433 GCG  GCA  GAG  TTC  GCG  GAG  GGT  AAA  GCA
123 Ala  Ala  Glu  Phe  Ala  Glu  Gly  Lys  Ala
                         125                     130
               GGA  GAG  GCT  AAG  GAT  GCC  ACA   480
               Gly  Glu  Ala  Lys  Asp  Ala  Thr   138
                                        135

481 AAG  TAG  GGT  CTT  ACC  TAA  TCA  GTT  AAT
139 Lys

TTC  AAG  CAC  TTA  AAC  TCG  TAG   528

529 ATA  TAT  TGA  TCC  ATA  TCC  TCT  CTC  TTC
               ATG  TTT  AAT  AGT  ACT  TAC  AAT   576
577 AAG  ATG  AGT  CTG  TTG  TAA  TTT  CTA  TTA
               ATT  TCA  CAT  CAC  AAC  TGA  AAT   624
625 AAG  ATA  TGG  TAT  CCA  CAG  TCA  CCG  TCA
               CAT  TCT  TTA  ATG  TTT  TGC  AAA   672
673 ATA  TTC  AAT  AGA  CAA  ATT  AAA  TAA  AAA
                                 AAA  AAA  AAA
``` as set forth in SEQ ID NO:1.

2. A plasmid referred to as pLCT10B and deposited as ATCC 75139 and containing the sequence set forth in claim 1.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 708
( B ) TYPE: nucleotides
( C ) STRANDEDNESS: Single
( D ) TOPOLOGY: Linear ( i i ) MOLECULE TYPE:
( A ) DESCRIPTION: cDNA ( i i i ) HYPOTHETICAL: No ( i v ) ANTI-SENSE: No ( v i ) ORIGINAL SOURCE:
( A ) ORGANISM: Arabadopsis
( B ) STRAIN: thaliana
( C ) INDIVIDUAL ISOLATE: pLCT10B
( G ) CELL TYPE: N/A ( i x ) FEATURE:
( A ) NAME/KEY: cDNA of COR15
( B ) LOCATION: Encoded by nucleic acids 55
to 139 of cDNA of Arabidopsis
thaliana and encoded polypeptide
( C ) IDENTIFICATION METHOD: Sequencing
( D ) OTHER INFORMATION: Encodes protectant polypeptide ( x i ) SEQUENCE DESCRIPTION: SEQ ID NO:1:

```
AAA AAC TCC TCC TTT CAT TTC CAA ACA AAA ACT TCT TTT TAT TCT CAC   48
ATC TTA AAG ATC TCT CTC ATG GCG ATG TCT TTC TCA GGA GCT GTT CTC   96
                        Met Ala Met Ser Phe Ser Gly Ala Val Leu
                                         5                    10

ACT GGT ATG GCT TCT TCT TTC CAC AGC GGA GCC AAG CAG AGC AGC TTC  144
Thr Gly Met Ala Ser Ser Phe His Ser Gly Ala Lys Gln Ser Ser Phe
                 15                  20                  25

GGC GCT GTC AGA GTC GGC CAG AAA ACT CAG TTC GTC GTC GTT TCT CAA  192
Gly Ala Val Arg Val Gly Gln Lys Thr Gln Phe Val Val Val Ser Gln
             30                  35                  40

CGC AAG AAG TCG TTG ATC TAC GCC GCT AAA GGT GAC GGC AAC ATC CTC  240
Arg Lys Lys Ser Leu Lle Thr Ala Ala Lys Gly Asp Gly Asn Ile Leu
         45                  50                  55

GAT GAC CTC AAC GAG GCC ACA AAG AAA GCT TCA GAT TTC GTG ACG GAT  288
Asp Asp Leu Asn Glu Ala Thr Lys Lys Ala Ser Asp Phe Val Thr Asp
```

-continued

```
          60                      65                         70
AAA  ACA  AAA  GAG  GCA  TTA  GCA  GAT  GGT  GAG  AAA  GCG  AAA  GAC  TAC  GTT   336
Lys  Thr  Lys  Glu  Ala  Leu  Ala  Asp  Gly  Glu  Lys  Ala  Lys  Asp  Tyr  Val
75                  80                       85                       90

GTT  GAA  AAA  AAC  AGT  GAA  ACC  GCA  GAT  ACA  TTG  GGT  AAA  GAA  GCT  GAG   384
Val  Glu  Lys  Asn  Ser  Glu  Thr  Ala  Asp  Thr  Leu  Gly  Lys  Glu  Ala  Glu
                    95                       100                      105

AAA  GCT  GCG  GCG  TAT  GTG  GAG  GAG  AAA  GGA  AAA  GAA  GCC  GCA  AAC  AAG   432
Lys  Ala  Ala  Ala  Tyr  Val  Glu  Glu  Lys  Gly  Lys  Glu  Ala  Ala  Asn  Lys
                    110                      115                      120

GCG  GCA  GAG  TTC  GCG  GAG  GGT  AAA  GCA  GGA  GAG  GCT  AAG  GAT  GCC  ACA   480
Ala  Ala  Glu  Phe  Ala  Glu  Gly  Lys  Ala  Gly  Glu  Ala  Lys  Asp  Ala  Thr
               125                      130                 135

AAG  TAG  GGT  CTT  ACC  TAA  TCA  GTT  AAT  TTC  AAG  CAC  TTA  AAC  TCG  TAG   528
Lys

ATA  TAT  TGA  TCC  ATA  TCC  TCT  CTC  TTC  ATG  TTT  AAT  AGT  ACT  TAC  AAT   576
AAG  ATG  AGT  CTG  TTG  TAA  TTT  CTA  TTA  ATT  TCA  CAT  CAC  AAC  TGA  AAT   624
AAG  ATA  TGG  TAT  CCA  CAG  TCA  CCG  TCA  CAT  TCT  TTA  ATG  TTT  TGC  AAA   672
ATA  TTC  AAT  AGA  CAA  ATT  AAA  TAA  AAA  AAA  AAA  AAA                       708
```